United States Patent [19]

Barmentlo et al.

[11] Patent Number: 5,258,188
[45] Date of Patent: Nov. 2, 1993

[54] PROCESS OF PREPARING A TEA PRODUCT

[75] Inventors: Bart Barmentlo, Delft; Willem J. Bel, Rotterdam, both of Netherlands; Bruin Hoogstad, Bedford; Sidney Pendlington, Stevington, both of Great Britain; Nigel K. Slater, Maasdam, Netherlands

[73] Assignee: Thomas J. Lipton Co., Division of Conopco, Inc., Englewood Cliffs, N.J.

[21] Appl. No.: 33,949

[22] Filed: Mar. 10, 1993

Related U.S. Application Data

[63] Continuation of Ser. No. 783,719, Oct. 25, 1991, abandoned, which is a continuation of Ser. No. 503,658, Apr. 3, 1990, abandoned.

[30] Foreign Application Priority Data

Apr. 6, 1989 [EP] European Pat. Off. .......... 89200865

[51] Int. Cl.$^5$ ............................... A23F 3/20
[52] U.S. Cl. ..................... 426/52; 426/597; 426/422
[58] Field of Search .......... 426/52, 422, 597

[56] References Cited

U.S. PATENT DOCUMENTS 3,959,497 5/1976 Takino .................. 426/52
4,004,038 1/1977 Wickremasinghe .......... 426/422

FOREIGN PATENT DOCUMENTS 0256567 2/1988 European Pat. Off. .
1380135 1/1975 United Kingdom .
1413351 11/1975 United Kingdom .
2057849 4/1981 United Kingdom .

OTHER PUBLICATIONS

Journal of Food Science, vol. 50, pp. 1126-1129, 1985.
Japanese patent Appln. JP 63-036,745 (Abstract).
Food Science and Technology Abstracts (FSTA), vol. 16, No. 4 (1984) (Abstract-No. 4H910).

Primary Examiner—Joseph Golian
Attorney, Agent, or Firm—James J. Farrell

[57] ABSTRACT

In a process of preparing a tea extract, the extract is adjusted to 20°-80° C., treated with tannase at pH=4-7 and then subjected to ultrafiltration at 2°-90° C. using a membrane with an average molecular weight exclusion point of at least 5000 Daltons (preferably at least 30,000 Daltons). The extract may finally be subjected to an additional filtration, preferably microfiltration. Also an instant a cold-water soluble tea powder or granulate is claimed.

14 Claims, No Drawings

PROCESS OF PREPARING A TEA PRODUCT

This is a continuation of Ser. No. 07/783,719, filed Oct. 25, 1991, now abandoned, which in turn is a continuation of Ser. No. 07/503,658, filed Apr. 3, 1990, now abandoned.

The present invention relates to a process of preparing a tea extract of improved colour without turbidity. The invention also relates to a cold water-soluble instant tea powder or granulate or tea extract prepared by the process of the present invention.

The manufactured teas available on the market are usually divided into some groups, which are distinguished essentially based on the activity of tea enzymes in the course of raw tea treatment. If the enzyme activity is caused to stop at a very early stage of tea processing, then substantially unfermented or green tea is the result. A partial action of the enzymes in processing yields a yellow tea, a still greater action yields red or oolong tea and if the tea leaves are subjected to withering, rolling and sorting, almost complete fermentation, firing and final sorting, then the conventional black tea is obtained.

Black tea extracts are normally produced by a hot or boiling water extraction process, usually a countercurrent process. However, the black tea extracts, and particularly dried black tea extract, when made to beverage concentrates, usually become turbid if the beverage or the extract is allowed to cool to room temperature or lower.

This turbidity is caused by material present in the original black tea (tea solids which are extracted by hot water, but which are insoluble in cold water). This precipitate, known as "tea cream", is separated from the infusion, for example by centrifugation. This clouding or creaming, however, has been a serious problem in the preparation of a stable commercial tea concentrate and in the acceptance by the consumer of soluble instant tea powders, particularly of instant ice tea products.

It has been proposed, e.g. in British Patents GB-B-1,413,351 and GB-B-1,380,135 (Unilever) to remove this tea cream or to solubilize the cold water-insoluble constituents of a hot water extract of tea by treating the tea with the enzyme tannase, either in free form or fixed to an insoluble matrix.

Although the tannase treatment does give a certain amount of solubilisation of the tea cream constituents, the extract is still turbid at 5° C.

The main disadvantage of this method is that the tannase comes into the tea and it has to be inactivated by a heat treatment, which is detrimental to the quality of the treated tea, or by a precipitation method which also impairs the quality of the tea.

It has further been proposed in Japanese patent application JP-A-63036745 (Potsuka Corp) to remove the tea cream from an extract of black tea by subjecting the extract to ultrafiltration at a temperature in the range of 5° C. to 15° C. The disadvantage of this method is the very low yield of this method.

Moreover, in the ultrafiltration the tea cream constituents to a certain extent are removed from the tea extract, but the results are not optimal, since also in this case the extract obtained is still turbid at 5° C.

It has now been found that the disadvantages of the prior art processes can be avoided by a method in which a tea extract, preferably a hot water tea extract, is first treated with tannase and subsequently subjected to ultrafiltration, optionally followed by a second filtration, preferably microfiltration.

It has also been found that this method yields a product, which upon drying gives a tea extract powder with excellent cold water solubility.

The present invention therefore relates to a process of preparing a tea extract, which comprises:

(a) preparing a tea extract, (b) adjusting the temperature of the extract to a value of from 20° C. to 80° C., (c) treating the extract with tannase while maintaining said temperature for a time sufficient to solubilize a substantial portion of the tea cream therein at a pH value between 4.0 and 7.0.

(d) subjecting the extract to an ultrafiltration treatment at a temperature of from 2° C. to 90° C., using a membrane having an average molecular weight exclusion point of at least about 5,000 Daltons so as to obtain a retained fraction and a permeate fraction, and (e) recovering the permeate fraction.

In the present invention, the use of a hot water extract is preferred. Also the use of black tea is preferred.

Normally, hot water extracts are prepared by extracting the tea with hot or boiling water (90°-100° C.) for a period of up to 15 minutes, but of course any suitable temperature-time relationship leading to a commercially satisfactory quality and yield may be used. The obtained hot tea extract is then cooled to a temperature, which makes it suitable for the tannase treatment.

The enzyme tannase, which is used in the present invention, is known to hydrolyze the galloyl ester linkages of polyphenolic substrates such as tannic acid, tea polyphenol gallates, and the like. It also attacks gallic acid methyl ester. One source of the enzyme is an elaboration product of the growth of certain moulds belonging to the genus Aspergillus or Penicillium, for example *Aspergillus niger*, *Aspergillus flavus*, or *Aspergillus oryzae*. For example *Aspergillus flavus* grown on a medium containing tannic acid as a sole carbon source provides tannase in substantial amounts. Two specific strains of microorganisms known to produce substantial quantities of tannase are *Aspergillus oryzae*, ATCC No 9362 and *Aspergillus niger*, ATCC No. 16888. One suitable preparation of tannase enzyme, obtained with a strain of *Aspergillus oryzae*, is commercially available as a powder under the name Tannase S (Trade Mark) from the Enzyme Development Corporation (New York N.Y.). Also Tannase R (Trade Mark) of the same company can be used.

The method used for the determination of tannase activity of enzyme preparation is a modification of the method described by R. L. Thomas and K. Murtagh in Journal of Food Science, Volume 50, 1126-1129 (1985).

This method determines the initial rate of production of free gallic acid from a substrate in the presence of tannase at 35° C. in a pH stat equipment. The modifications are the use of a different substrate, viz. a 0.4% by weight solution of tannic acid (ex Sigma Chemical Company, St. Louis, USA, Lot-no 87F-0745) and a different pH, viz. the end point setting of the pH value is 5.5.

According to this method the Tannase S powder has about 4200 enzyme units per gram of powder. The accuracy of the method is 5%.

The enzyme preparation can be in soluble or insoluble powder form, or in solution, or immobilised on a solid support to allow its removal from the system and re-use of the enzyme.

The tea treatment step with tannase may be carried out, using a range of enzyme concentrations, temperatures and incubation times.

The temperature at which the treatment is carried out may, dependent on the tannase type, vary from 20° C. to 80° C. At the higher limits of the range a less desirable conversion is obtained. Very favourable yields are obtained at a temperature within the range of 40° C. to 70° C.

The incubation time depends on the enzyme concentration and the temperature and may vary from a few minutes to several hours at lower temperatures.

An enzyme level ranging from about 0.5 to 500 or more tannase units (determined as hereinbefore described) per gram dry weight of tea may be used. An enzyme level of about 20 tannase units per gram dry weight of tea gives very satisfactory results. Higher levels of enzyme permit shorter treatment times, but are also more expensive. In a preferred embodiment of the present invention, the tannase is recycled and in that case higher initial levels of tannase are used.

During the tannase treatment the pH drops and therefore the pH is adjusted, preferably before the conversion step to a value between 4.0 and 7.0, with a preferred pH being in the range 4.5 to 6.0.

Preferably the tannase treatment is carried out with continuous stirring of the tea extract in a series of tank reactors, in which the first vessel is continuously fed with fresh tea extract and tannase, while decreamed tea extract is removed from the last reactor and the tannase is recycled.

The tea extract which has been treated with tannase is subsequently subjected to an ultra-filtration (hereafter referred to as UF) treatment. The conditions of this UF treatment are those conventionally used and are selected such that the extract is handled as carefully as possible.

The temperature at which the UF treatment is carried out is from 2° C. to 90° C., preferably from 5° C. to 40° C. The pressure in the UF treatment is generally of the order of up to 30 bar, preferably from 1 to 15 bar. The membranes used may be those conventional in the art, for example membranes of polysulphones or cellulose acetate, either in flat membrane form, tubular form, and the like. Preferably, however, tubular ceramic membranes are used. The membrane should have an average molecular weight exclusion point of at least 5,000 Daltons, preferably of at least 30,000 Daltons and most preferably of from 30,000 to 500,000 Daltons. If the membrane has a molecular weight exclusion point below 5,000 Daltons, then the yield of the treatment is economically unacceptable.

A suitable UF device is for example a module equipped with Romicon XM 50 membranes of the polyacrylonitrile type having an average molecular exclusion point of 50,000 Daltons.

Although in principle a good quality of tea extract is obtained by the combination of treating tea extract with tannase followed by an UF treatment, it has been found advantageous to subject the permeate obtained in the UF treatment to an additional filtration treatment, preferably a microfiltration (hereafter referred to as MF) treatment.

To this purpose the temperature of the tea extract obtained from the UF treatment is preferably adjusted to within the range of 0° C. to 20° C. after which the tea extract is subjected to the additional filtration treatment, preferably a MF treatment using a MF device having a mean pore size of from 0.01 to 100 micron, the pore size used being dependent on the cooling method. The obtained tea extract is then concentrated or dried in a manner known per se, for example by spray drying, or freeze drying, optionally preceeded by a concentration treatment, e.g. a reverse osmosis treatment.

Preferably the obtained tea extract is converted into a powder by the method as described in European Patent Application EP-A-0,256,567 (Unilever) i.e. the tea extract is concentrated and frozen in a continuous layer having a thickness of from 0.2 to 5.0 mm in a time between 3 and 100 seconds, after which the concentrated frozen tea extract is freeze-dried.

The invention is now illustrated by the following examples which are not to be construed as limiting the scope of the present invention.

EXAMPLE I

3 Kg of a black tea blend were mixed with 40 liters of distilled water of 95° C. while continuously stirring. The extraction was continued for 5 minutes at 95° C., after which the leaves were filtered off using a 100 mesh screen with a surface of 0.2 m$^2$.

An extract was obtained with 2.25% by weight of tea solids, which was subsequently cooled to 45° C. Tannase (with a strength of 1200 tannase units per gram, determined as described hereinbefore and obtained from *Aspergillus niger*, ex Novo Industrie A/S) was added in an amount of 1 gram/liter of tea extract and the tea extract wa incubated for 45 minutes at 45° C. whilst stirring. The pH of the extract was adjusted to 5.0 by addition of sodium hydroxide during the tannase treatment.

When the tannase treated tea extract was cooled to 5° C. a precipitate formed with a turbid supernatant, thus demonstrating, that the tannase treatment alone does not yield satisfactory products.

The obtained, treated tea extract was now treated by UF in a module equipped with Romicon HF26.5-43-PM30 polyacrylonitrile membranes having an average molecular weight exclusion point of 50,000 Daltons at 45° C. and an area of 26.5 ft$^2$ (2.46 m$^2$). The UF treatment was continued until 20 liters of a tea extract were obtained with 1.85% by weight of tea solids.

The clear solution obtained was subsequently cooled to 5° C., upon which a precipitate formed. The extract with the precipitate was subjected to a filtration treatment at 5° C., using filter paper with a gram weight of 68 g/m$^2$, ash content 0.1% and a filtration time according to German Industrial Standard DIN 53137 of 12–40 seconds (ex Schleicher and Schüll, W-Germany), after which a very clear tea extract was obtained with 1.84% by weight of tea solids. Upon cooling to 5° C. this extract remained crystal clear.

If the tea extract obtained before the tannase treatment was subjected to the UF treatment as described above, an extract was obtained which was still turbid, thus showing that the UF treatment alone does not lead to acceptable products either.

EXAMPLE II

1 Kg of a black tea blend were mixed with 13 liters of distilled water of 95° C. whilst continuously stirring. The extraction was continued for 5 minutes at 95° C., after which the leaves were filtered off as described in Example I, upon which an extract with 2.15% by weight of tea solids was obtained.

The extract was cooled to 45° C. and the same tannase enzyme as described in Example I was added in a quantity of 1 gram tannase per liter of tea extract. The incubation time was 45 minutes at 45° C. whilst stirring. The obtained, treated extract was now subjected to UF in a module equipped with a surface of 5 ft$^2$ (0.456 m$^2$), Romicon HF5-43-PM 10 membranes having an average molecular weight exclusion point of 10,000 Daltons, at 20° C. The UF treatment was continued until 4 liters of extract were obtained, having 0.70% by weight of tea solids.

The extract upon cooling to 5° C. remained crystal-clear.

EXAMPLE III

Example I was repeated, but now using a commercial green tea blend. After the extraction with hot water an extract was obtained with 1.22% by weight of tea solids. The tannase used was Tannase S (ex Enzyme Development Corporation, New York, USA) in an amount of 1 mg/liter of tea extract, the enzyme having a strength of 4200 tannase units per gram, determined as hereinbefore described.

The UF treatment was carried out using a module with Romicon HF1-43-PM 500 membranes with a surface of 1 ft$^2$ (0.093 m$^2$) having an average molecular weight exclusion point of 500,000 Daltons. The extract obtained had 1.04% by weight of tea solids and remained perfectly crystal-clear upon cooling to 5° C.

EXAMPLE IV

12 Kg of a commercial black tea blend were continuously extracted with 120 liters of demineralized water of 60° C. at a flow rate of 4 l/min, to obtain after filtration 120 liters of tea extract with 3.46% by weight of solids.

The extract was cooled to 45° C. and was subsequently treated batchwise (in portions of 50 liters) with 0.24 g/l of tannase (as usual in Example I) for 45 minutes per batch while stirring. The pH of the extract was adjusted to 5.0 by addition of potassium hydroxide. The obtained, treated tea extract was now subjected to an UF treatment at 45° C. by recirculating it over a module, equipped with Romicon HF26.5-43-PM30 polysulphone membranes, having an area of 2.5 ft$^2$ (0.23 m$^2$) and an average molecular weight exclusion point of 30,000 Daltons. Per batch of 50 liters, 45.7 liters of extract with 2.37% by weight of tea solids were obtained.

This extract was concentrated by reverse osmosis at a temperature of 35° C. and a pressure of about 35 bar. The resulting concentrated tea extract contained 12.5% by weight of tea solids. The tea concentrate was subsequently frozen in a drum-type freezer in layers with an average thickness of about 1 mm at a temperature of −8° C. at a rate of 3.5 g/sec. The freezing time was approximately 20 seconds. The frozen layer was removed from the drum and disrupted into discrete particles with an average size of about 1 mm×3 mm×3 mm. The obtained particles were subsequently freeze-dried at a temperature of 30° C. and a pressure of 100 mbar.

A light tea granulate was obtained, which quickly dissolved in demineralized water of 0° C., yielding a crystal-clear solution.

We claim:
1. In an improved process of preparing a final tea extract, comprising the steps of:
 (a) preparing a tea extract,
 (b) adjusting the temperature of the extract to a value of from 20° C. to 80° C.,
 (c) treating the extract with tannase while maintaining said extract temperature at 20° C. to 80° C. for a time sufficient to solubilize a substantial portion of the tea cream therein at a pH value between 4.0 and 7.0; wherein the improvement comprises
 (d) subjecting the treated extract to an ultrafiltration treatment at a temperature of from 2° C. to 90° C. using a membrane having an average molecular weight exclusion point of at least 5,000 Daltons so as to obtain a retained fraction containing said tannase and a permeate fraction,
 (e) recovering the permeate fraction,
 (f) adjusting the temperature of the permeate fraction to within the range of from 0° C. to 20° C., and
 (g) subjecting the permeate fraction to a filtration treatment to obtain a tea extract which remains clear upon cooling to 5° C., and
 (h) recycling the retained fraction from step (d) into the tannase treatment step (c) to assist in treating further tea extract.

2. A process according to claim 1, in which the filtration treatment of step (g) is accomplished using a microfiltration device having a mean pore size of from 0.01 to 100 micron.

3. A process according to claims 1, in which the finally obtained extract is subjected to the steps of:
 (h) concentrating the tea extract, preferably by reverse osmosis,
 (i) freezing the concentrated tea extract in a continuous layer having a thickness of from 0.2 to 5.0 mm in a time between 3 and 100 seconds, and
 (j) freeze-drying the concentrated frozen tea extract.

4. A process according to claim 1, in which in step (a) the extract is a hot water extract.

5. A process according to claim 1, in which in step (b) the temperature is adjusted to within the range of 40° C. to 70° C.

6. A process according to claim 1, in which in step (c) the pH is adjusted to a value between 4.5 and 6.0.

7. A process according to claim 1, in which step (c) from 0.5 to 500 tannase units per gram dry weight of tea are used.

8. A process according to claim 1, in which in step (c) the tannase treatment is carried out in a series of stirred tank reactors with recycling of the tannase.

9. A process according to claim 1, in which in step (d) the UF treatment is carried out at a temperature in the range of 5° C. to 40° C.

10. A process according to claim 1, in which in step (d) the membrane has an average molecular weight exclusion point of at least 30,000 Daltons.

11. A process according to claim 1, in which in step (d) the membrane has an average molecular weight exclusion point of from 30,000 to 500,000 Daltons.

12. A process according to claim 1, in which in step (d) the pressure is u to 30 bar.

13. A process according to claim 1, in which in step (d) the pressure is from 1 to 15 bar.

14. A process according to claim 1, in which the tea extract is a black tea extract.

* * * * *